US00PP09533P

United States Patent [19]

Schumann

[11] Patent Number: Plant 9,533

[45] Date of Patent: Apr. 30, 1996

[54] GERANIUM PLANT NAMED 'FISRAIN'

[75] Inventor: Ingeborg Schumann, Albstadt, Germany

[73] Assignee: Florfis AG, Binningen, Switzerland

[21] Appl. No.: 360,347

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium named Fisrain, particularly characterized by the combined features of single flower form, light violet flower color, purple veins on upper petals, intense green leaves with strong zonation, vigorous growth habit and good branching ability, and medium to late flower response.

2 Drawing Sheets

The present invention comprises a new and distinct cultivar of geranium, botanically known as *Pelargonium, peltatum l'Hert,* commonly referred to as ivy geranium, and referred to by the cultivar name Fisrain.

Fisrain is a product of a planned breeding program which had the objective of creating new ivy geranium cultivars with single flowers and a well-branched plant habit, and in various flower colors.

Fisrain was originated from a hybridization made by inventor Ingeborg Schumann in a controlled breeding program in Galdar, Gran Canaria, Spain in 1987. The female parent was a chance seedling of the variety Etincelant, having single, light violet flowers and foliage with strong zonation and medium growth. By comparison, Etincelant is characterized by semi-double red flowers and vigorous growth. The male parent of Fisrain was the cultivar Amethyst, characterized by its large double violet colored flowers, compact plant habit, and very late flower response.

Fisrain was discovered and selected as one flowering plant within the progeny of the stated cross by Ingeborg Schumann in 1988 in a controlled environment in Galdar, Gran Canaria, Spain.

The first act of asexual reproduction of Fisrain was accomplished when vegetative cuttings were taken from the initial selection in autumn 1989 in a controlled environment in Galdar, Gran Canaria, Spain, by, or under the supervision of, Ingeborg Schumann.

Horticultural examination of plants grown from these cuttings initiated in May 1990, and continuing thereafter, has demonstrated that the combination of characteristics as herein disclosed for Fisrain are firmly fixed and are retained through successive generations of asexual reproduction.

Fisrain has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisrain, which, in combination, distinguish this geranium as a new and distinct cultivar:

1. Single flower form.
2. Light violet flower color.
3. The upper flower petals have purple veins.
4. Intense green leaves with strong zonation.
5. Vigorous growth habit and good branching ability.
6. Medium to late flower response.

There are no commercial cultivars to which Fisrain can be closely compared. In comparison to the male parent Amethyst, Fisrain has single flowers and a lighter violet flower color, much more vigorous growth habit, and a little earlier flowering.

The accompanying color photographic drawings show typical flower and foliage characteristics of Fisrain, with colors being as true as possible with illustrations of this type.

The photograph on sheet 1 is of a plant of Fisrain in a hanging basket.

The photograph on sheet 2 shows a plant of Fisrain in a pot, with the umbels and foliage being shown in more detail.

In the following description, color references are made to The Royal Horticultural Society Colour Chart. The color values were determined indoors in May from plants grown indoors in Hillscheid, Federal Republic of Germany.

Classification:

*Botanical.*—A hybrid of the species *Pelargonium peltatum l'Hert.*

*Commercial.*—Ivy geranium, cv., Fisrain.

INFLORESCENCE

Umbel:

*Shape.*—Irregular.

*Average diameter.*—105 mm.

*Average depth.*—50 mm.

*Peduncle length.*—150 mm.

*Pedicel length.*—38 mm.

*Pedicel color.*—Green infused with red.

*Number of flowers per umbel.*—5–6.

Corolla:

*Average diameter.*—52 mm long, 44 mm wide.

*Form.*—Single, zygomorph.

*Number of petals.*—5.

*Number of petaloids.*—None.

*Color (general tonality from a distance of three meters).*—Light violet.

*Color of upper petals.*—78C.

*Color of lower petals.*—78C, with no markings.

*Markings on upper petals.*—There are two distinct purple streaks (74A) on the upper surface of the upper petals, and a much weaker purple marking (similar to main color 78C) between the streaks. The darker purple veins are approximately 74A.

*Color of lower surface of petals.*—77D-78D, with similar but lighter purple streak markings which branch and diminish near upper ends.

*Color of sepals.*—Medium green, largest sepal with anthocyanin.

*Number of sepals.*—5.

Bud:

*Shape.*—Narrow, elliptical.

*Color (adaxial).*—Medium green.

*Color (abaxial).*—Light violet.

Reproductive organs:

*Androecium.*—7 fertile anthers, white filaments, orange pollen.

*Gynoecium.*—5–6 lobed stigma, violet pink.

Spring flowering response period: In Hillscheid, Federal Republic of Germany, in 1993 plants had on average 0.8 flowers opened 15 weeks after planting of unrooted cuttings (pinched plants).

Outdoor flower production: The flower count in 1993 in Hillscheid, Federal Republic of Germany was between 48 and 52 umbels per plant for May through August observation period.

Seeds: Seed set can occasionally be observed but never so much that it affects the development of new umbels.

Durability: Average for single flowered varieties.

PLANT

Foliage:

*Form.*—Ivy-shaped.

*Margin.*—Entire.

*Size of leaf.*—8 cm.

*Color of upper surface.*—Medium green, approximately 137B.

*Color (zonation).*—Brown 166A.

*Tolerance of botrytis.*—Good, due to smooth surface of leaf.

General appearance and form:

*Internode length.*—4–6 cm.

*Branching pattern.*—3.5 branches per week.

*Length.*—95 cm (in September, 35-week-old plants).

It is claimed:

1. A new and distinct cultivar of geranium plant named Fisrain, as illustrated and described.

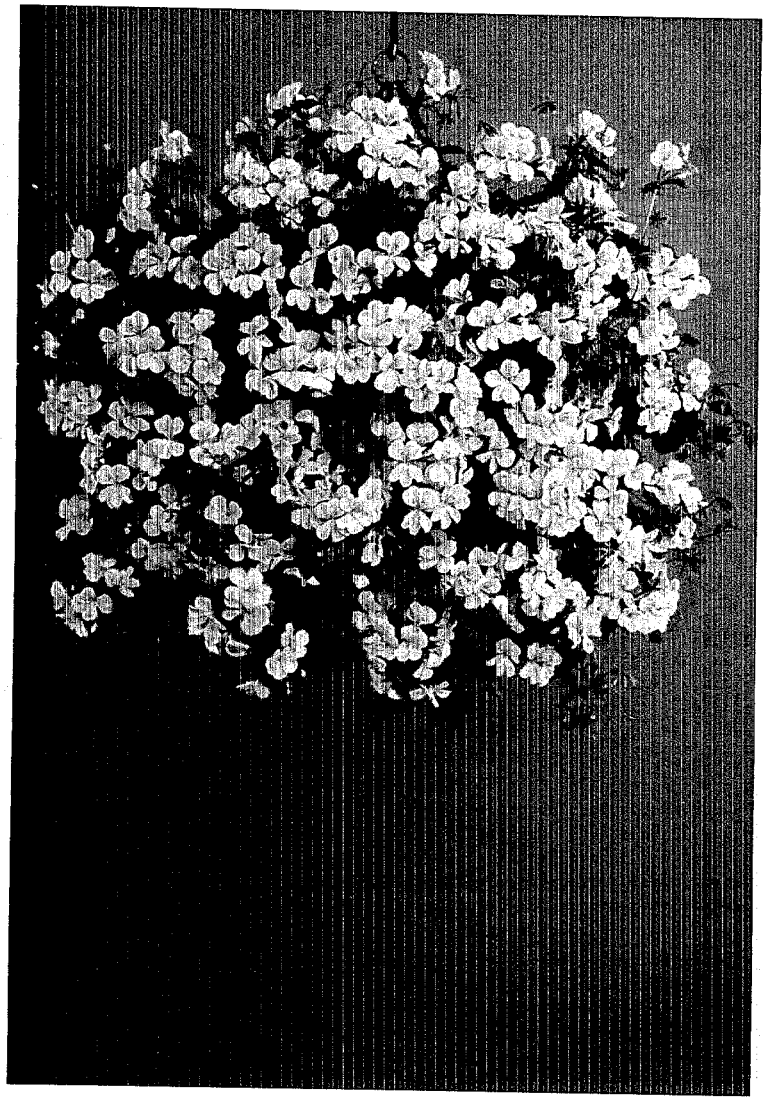

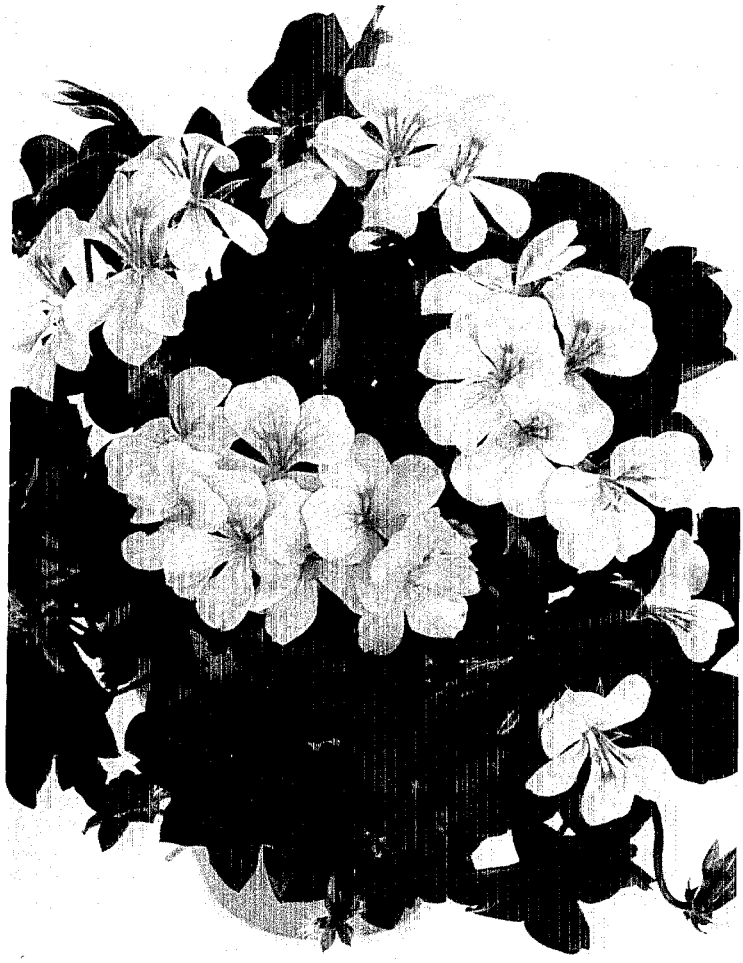

* * * * *